(12) United States Patent
Tartare-Deckert et al.

(10) Patent No.: US 7,651,844 B2
(45) Date of Patent: Jan. 26, 2010

(54) METHOD FOR SCREENING AGENTS CAPABLE OF TREATING OBESITY

(75) Inventors: Sophie Tartare-Deckert, Nice (FR); Emmanuel Van Obberghen, Nice (FR)

(73) Assignees: Merck Sante, Lyons (FR); Institut National de la Sante et de la Recherche Medicale (INSERM), Paris (FR)

( * ) Notice: Subject to any disclaimer, the term of this patent is extended or adjusted under 35 U.S.C. 154(b) by 458 days.

(21) Appl. No.: 10/416,444

(22) PCT Filed: Nov. 8, 2001

(86) PCT No.: PCT/FR01/03473

§ 371 (c)(1),
(2), (4) Date: Oct. 23, 2003

(87) PCT Pub. No.: WO02/38807

PCT Pub. Date: May 16, 2002

(65) Prior Publication Data

US 2004/0049799 A1    Mar. 11, 2004

(30) Foreign Application Priority Data

Nov. 10, 2000   (FR)  .................................. 00 14487

(51) Int. Cl.
*G01N 33/53* (2006.01)
*A01N 1/02* (2006.01)
*C12Q 1/68* (2006.01)

(52) U.S. Cl. .............................. 435/7.8; 435/7.1; 435/6; 435/2

(58) Field of Classification Search ........................ None
See application file for complete search history.

(56) References Cited

U.S. PATENT DOCUMENTS 6,054,485 A * 4/2000 Schwartz et al. ............ 514/568
6,239,326 B1 * 5/2001 Howe .......................... 800/18

FOREIGN PATENT DOCUMENTS

WO  WO 98 20112   5/1998
WO  WO 98 29138   7/1998

OTHER PUBLICATIONS

Jandeleit-Dahm et al., Micro Res Jan. 2000 59:61-71.*
Koppelman P. 2000, Nature 404:635-643.*
Brekken et al. 2000, Matrix Biology 19:569-580.*
Gronthos et al. 2001, J Cell. Physiol. 189:54-63.*
Takahashi et al. 2001, Obesity Research 9:388-393.*
Bradshaw et al. 2003. PNAS 100:6045-6050.*
Delaney et al. 2003. Endocrinology 144:2588-2596.*
Jandeleit-Dahm et al. 2000, Microvasc. Res. 59:61-71.*
Haynes et al. 1998. Electrophoresis 19:1862-1871.*
Opara et al 1997. Southern Medical Journal 90:1162-1168.*
Walley et al. 2006. Human Molecular Genetices 15(2):R124-R130.*
Maeda et al 1997. Gene 190:227-235.*
Jandeleit-Dahm K et al:, "SPARC gene expression is increased in diabetes-related mesenteric vascular hypertrophy", Microvascular Research, vol. 59, No. 1, Jan. 2000, pp. 61-71, XP001010337 the whole document.
Tartare-Deckert S et al:, "The matricellular protein sparc/osteonectin as a newly identified factor up-regulated in obesity", Journal of Biological Chemistry, vol. 276, No. 25, Jun. 22, 2001, pp. 22231-22237, XP001010354, the whole document.
Ledda M F et al:, "Suppression of SPARC Expression by Antisense RNA Abrogates the Tumorigenicity of Human Melanoma Cells", Nature Medicine, Nature Publishing, CO, US, vol. 3, No. 2, Feb. 1, 1997, pp. 171-176, XP002061780, ISSN: 1078-8956, the whole document.
Graham JD et al:, "Expression of Osteonectin mRNA in Human Breast Tomours is Inversely Correlated with Oestrogen Receptor Content", European Journal of Cancer, Pergamon Press, Oxford, GB, vol. 33, No. 10, Sept. 1997, pp. 1654-1660, XP004284400, ISSN: 0959-8049, the whole document.

* cited by examiner

*Primary Examiner*—Manjunath N Rao
*Assistant Examiner*—Shulamith H Shafer
(74) *Attorney, Agent, or Firm*—Young & Thompson

(57) ABSTRACT

The invention concerns a method for screening agents capable of treating, by way of prevention or cure, obesity or one of the disorders associated with obesity by modulating the expression of the SPARC protein or of its activity. The invention also concerns a method for diagnosing obesity or one of the disorders associated with obesity by monitoring the expression rate of the SPARC protein or its activity. The invention further concerns a composition comprising an agent modulating the expression of the SPARC protein or its activity. The invention finally concerns the use of any agent modulating the expression of the SPARC protein or its activity for preparing a pharmaceutical composition for treating, by way of prevention or cure, obesity or one of the disorders associated with obesity.

5 Claims, No Drawings

METHOD FOR SCREENING AGENTS CAPABLE OF TREATING OBESITY

The subject of the present invention is a method for screening agents capable of treating, preventively or curatively, obesity or one of the disorders associated with obesity. It also relates to a method for diagnosing. obesity or one of the disorders associated with obesity by monitoring the expression of the SPARC protein or its activity. It also relates to a composition comprising at least one agent modulating the expression or the activity of the SPARC protein. It also relates to the use of any agent modulating the expression or the activity of the SPARC protein for the preparation of a pharmaceutical composition intended for treating, preventively or curatively, obesity or one of the disorders associated with obesity.

Obesity results from a positive long-term imbalance between the energy taken in and the energy expended. Obesity is a major physiopathological disorder which may be associated with numerous diseases, such as cardiovascular disorders, including hypertension and atherosclerosis, metabolic disorders such as diabetes, hyperinsulinemia, insulin resistance and certain types of cancer. In the United States, it is estimated that more than 30% of the adult population is obese, that is to say has a weight of more than 20% above the estimated normal weight. Numerous indications tend to prove that obesity is becoming a worldwide health problem.

It is accepted that the weight of a body is determined by multiple interactions between genes and environmental factors, such as diet, psychological states and frequency of physical activity. It is accepted that, in numerous cases, a diet and physical exercise are not sufficient for losing weight; this is all the more true for people who are genetically predisposed to becoming obese. Many genes indeed appear to contribute to the pathogenesis of obesity. Thus, it has recently been possible to identify genes specific for obesity in humans. However, the mutations identified up until now allow only a minimum proportion of the syndromes of obesity to be explained.

Consequently, it has proved necessary to analyze the specific expression of genes in the adipose tissue which can explain the mechanisms contributing to this deregulation in obese people. The genes exhibiting an impaired expression can thus be a target particularly suitable for the diagnosis or curative or preventive treatment of obesity.

Accordingly, after numerous studies, the authors of this invention have found that the SPARC protein (Secreted Protein Acidic and Rich in Cysteine, also known by the name osteonectin and BM-40) is secreted by the white adipocyte, that its expression is higher in "obese" mouse models than in "slim" mouse models and that its expression may be regulated according to the diet administered.

The SPARC protein is a glycoprotein associated with the extracellular matrix which is widely distributed in human tissues during development. It is described as regulating morphogenesis, cell proliferation and differentiation. Although its specific role still remains uncertain, its high degree of conservation between species suggests a high pressure for conserving it during evolution. In patent application WO98/20112, it is described that a transgenic mouse lacking the SPARC gene is susceptible to hyperglycemia. There is also described therein a method for treating disorders associated with an underexpression of SPARC, such as in particular diabetes, cataracts, osteoporosis and proteinuria, by introducing into the cells of the mammal affected by this disorder a polynucleotide encoding the SPARC protein.

The subject of the present invention is a method for screening agents capable of treating, preventively or curatively, obesity or one of the disorders associated with obesity, by modulating the level of expression or activity of the SPARC protein.

As regards the prevention of obesity, it may indeed be advantageous to treat using agents thus identified subjects who have been diagnosed as being predisposed to obesity before they take on too much weight.

More specifically, this method of screening comprises the following steps:
  measuring the level of expression or the activity of the SPARC protein in the presence and optionally in the absence of the agent to be tested,
  determining if the level of expression or the activity of the SPARC protein is modulated in the presence of the agent to be tested compared with a control,
  optionally, identifying the agent which modulates the level of expression of the activity of the SPARC protein.

Either the agent to be tested is directly administered by the enteral or parenteral route to the mammal, generally a non-human mammal, and then the measurement is carried out in or using a biological material from said mammal, such as a cell, a cellular extract, a body fluid, serum, plasma, a tissue or a tissue extract. Or the agent to be tested is brought into contact with a biological extract, such as in particular a cell, a cellular extract, a body fluid, serum, plasma, a tissue, a receptor or a tissue extract and the measurement is then carried out directly, the biological extract having been collected before said bringing into contact.

This level of expression or this activity may be measured using a biological extract, such as in particular a cell, a cellular extract, a body fluid, serum, plasma, a tissue, a receptor or a tissue extract. Of course, the extract or the material used should be capable of expressing or responding to an activity of the SPARC protein. Preferably, the extract or the material used is derived from an adipose tissue or a body fluid, such as serum or plasma. For example, in the case of cells, it is preferable to measure the expression or the activity of the SPARC protein in adipocytes or striated muscle cells. This measurement can therefore require collecting beforehand the organ or a portion of the organ from the mammal to be tested. Preferably, the organ or the portion of the organ removed comprises an adipose tissue. More particularly, the adipose tissue is an abdominal adipose tissue or skeletal muscle.

According to the following step, it is determined if the level of expression or the activity of SPARC is modulated. Thus, it is possible to analyze if it is increased or decreased in the presence of the agent to be tested compared with the same test in the absence of the agent to be tested (control). This modulation may also be determined over time. Thus, the agent to be tested may be, for example, added to the cells or administered to an animal or samples are collected successively over time in order to determine the variation over time of the expression or the activity of the SPARC protein. In this case, the control corresponds to a measurement of the level of expression or of the activity of the SPARC protein in the presence of the agent, but carried out at a different moment.

The expression or the activity associated with the SPARC protein may be modulated in various ways. The modulation of its expression may correspond to the modulation of the level of expression of the SPARC protein or of its gene. The activity of the SPARC protein corresponds more particularly to its actual biological activity or to its signaling, that is to say to the biological consequences which its biological activity causes. The modulation of its signaling may correspond to the modulation of a biological effect due to the SPARC protein, in particular by blocking an active site of the SPARC protein or by modifying its conformation, thus modulating one of its biological effects.

Thus, the methods of measurement which can be used are numerous and are those known to persons skilled in the art. There may be mentioned in particular the ELISA method (measuring the level of expression of the protein), the Northern blot or quantitative PCR (measuring the level of expression of mRNA) method of analysis, biochemical methods of analysis by measuring cell proliferation or differentiation, or by microscopic analysis on the morphogenesis of the tissue studied (in this case, a correlation between the morphogenesis of the biological tissue, material or extract, and the level of expression or the activity of the SPARC protein is to be made subsequently).

Preferably, the expression or the activity of the SPARC protein in circulation or of the adipose tissue is carried out.

If necessary, the nature of the agent which modulates according to the method of the present invention the expression or the activity of the SPARC protein is defined.

The authors of the present invention were therefore able to demonstrate that the expression of the SPARC protein is higher in "obese" mouse models than in "slim" mouse models. Given these results, it is possible to establish a relationship between agents capable of treating obesity and their capacity to reduce the expression or the activity of the SPARC protein. However, it is possible, as in the case of leptin which may be overexpressed in obese people, to envisage a treatment using the protein or an agent increasing its expression as a therapeutic agent.

Thus, the agent which increases or which decreases the level of expression or the activity of the SPARC protein can be used for treating obesity or one of the disorders associated with obesity, the obesity or one of the disorders associated with the obesity exhibiting an overexpression of this SPARC protein.

More particularly, these agents thus identified are capable of treating, preventively or curatively, obesity or one of the disorders associated with obesity, such as in particular hypertension, atherosclerosis, diabetes (generally type 2 diabetes), hyperinsulinemia, insulin resistance, or more globally insulin resistance metabolic syndrome (IRMS). Preferably, these agents are capable of preventively or curatively treating obesity.

The present invention also relates to the agents thus identified which modulate the expression or the activity of the SPARC protein as medicaments. Preferably, the expression or the activity of the SPARC protein corresponds to that of the SPARC protein in circulation or of the adipose tissue.

It also relates to an ex vivo method for diagnosing obesity (including predisposition to obesity) or one of the disorders associated with obesity by measuring the level of expression or activity of the SPARC protein. Thus, the SPARC protein becomes a diagnostic tool.

This diagnostic method can make it possible to monitor the progress of one of the disorders. Indeed, it can prove necessary, during a pharmaceutical treatment to monitor the process of one of these disorders through the monitoring of the level of expression or activity of the SPARC protein.

More particularly, this ex vivo method comprises the following steps:
measuring the expression or activity of the SPARC protein of a control or of a material to be diagnosed,
determining the modulation of the expression or activity of the SPARC protein of the material to be diagnosed compared with said control.

Thus, the control may be the material to be diagnosed but of which the measurement of the expression or the activity of the SPARC protein is carried out before or after measuring the expression or activity of the SPARC protein of the material to be diagnosed. There is thus a progress, over time, of the expression or activity of the SPARC protein. The control may be a human being not having one of these disorders. There is thus a direct comparison of the levels of expression or of the activity of the SPARC protein of a human being not having one of these disorders and of a human being to be diagnosed. Thus, if an increase in the level of expression or activity of the SPARC protein is observed on said material to be diagnosed, said material comes from an obese human being or at least predisposed to being obese or from a human being having one of the disorders associated with obesity. From these results, and carrying out this test several times spaced out over time, it is possible to monitor the progress over time of one of these diagnosed disorders, in particular with the aim of monitoring the efficacy or inefficacy of a treatment followed by this person.

The material to be diagnosed may be one of the biological materials collected, as described above, from a human being. The extract may thus be a cell, a cellular extract, a body fluid, serum, plasma, a tissue or a tissue extract. Of course, the material or the extract used should be capable of expressing or responding to an activity of the SPARC protein.

The measurement of the expression or activity of the SPARC protein is as described above.

The present invention also relates to a composition comprising, in a physiologically acceptable medium, at least one agent modulating the expression or the activity of the SPARC protein, this composition being particularly well suited to pharmaceutical use and more particularly to treating, curatively or preventively, obesity or a disorder linked to obesity.

In this context, the subject of the present invention is a method for producing a pharmaceutical composition comprising the use of the screening method as defined above and mixing the product identified with a pharmaceutically acceptable carrier.

It also relates to the use of any agent modulating the expression or activity of the SPARC protein for the preparation of a pharmaceutical composition intended for treating, preventively or curatively, obesity or one of the disorders associated with obesity.

It finally relates to the methods for treating, curatively or preventively, obesity or one of the disorders associated with obesity by administering, enterally or parenterally, a composition as described above.

Obesity or disorders linked to obesity are more particularly linked to an overexpression of the SPARC protein.

The expression enteral route is understood to mean more particularly the oral or rectal route. The expression parenteral route is understood to mean more particularly an injection or a topical application to the skin, in particular by means of a patch.

Preferably, the agent modulates the expression or the activity of the SPARC protein in circulation or in the adipose tissue.

Concrete but nonlimiting examples of the invention will now be presented.

EXAMPLES

To detect the changes in expression of mRNA in the white adipose tissue of the GTG obese mouse model, cloning by subtractive hybridization and suppressive PCR was carried out using, according to the manufacturer's protocol, the PCR-select cDNA subtraction kit (from the company Clontech, Palo Alto, Calif., USA).

The "goldthioglucose" (GTG) mouse model was obtained by administering "goldthioglucose" as a double injection into a three-week old OF-1 male mouse (from the company Iffa-Credo), as described in the publication by Marchand-Brustel Y. et al., (1978) Am. J. Physiol. 234: E348-358.

OF-1 male mice were used for comparison.

2 µg of mRNA from the epididymal white adipose tissue of 4 GTG "obese" mice (weight 60±3 g) are used as "tester" and 2 µg of MRNA from the epididymal white adipose tissue of 8 "thin" OF-1 mice (weight 35±2 g) as "driver".

After hybridization, differential transcripts were selectively amplified by suppressive PCR, as described in the publication by Diatchenko, L. et al., (1999): Methods Enzymol. 303: 349-80. The PCR products were subcloned into the vector pCR 2.1 using the TOPO TA cloning kit (Invitrogen, Groningen, The Netherlands). Transformed clones were randomly selected and the plasmids were purified using QIAprep columns (Qiagen).

Partial cDNA sequences were determined and compared with the aid of sequences available on the GenBank database and mouse EST (expressed sequence tag) databases using the BLAST programs for search for homology.

Thus, this analysis revealed a sequence precisely corresponding to that of the untranslated 3' region of the mouse SPARC gene (see Mason, I. J. et al., (1986) EMBO J.5: 1465-1472).

The full-length cDNA probe encoding the mouse SPARC protein was obtained by reverse-transcription (RT-PCR) from white adipose tissue using the RT-PCR kit in a Super-Script step according to the recommendations of the manufacturer (Life Technologies).

A Northern hybridization with a full-length cDNA probe encoding the SPARC protein confirmed the high level of the major SPARC transcript (2.2. kb) in the "obese" GTG mouse white adipose tissue, this level being 5 to 6 times as high as in the OF-1 "thin" mouse.

The expression of mRNA for SPARC was also examined in the liver and the skeletal muscle, two other tissues which respond to insulin and which are involved in the homeostasis of glucose.

In both types of mouse, no expression of SPARC was observed in the liver. By contrast, mRNA was detected in the muscles but at a lower level than in the adipose tissue. However, the quantity of mRNA from SPARC expressed in this tissue was equivalent in both types of mouse.

The expression of SPARC in various "thin" mouse tissues was also examined. It is found that the brown adipose tissue expresses mRNA for SPARC and that one of the major tissues expressing the SPARC transcripts in adult mice is the white adipose tissue.

The expression of mRNA from SPARC was also studied in ob/ob mouse and its "thin" control (respectively male mouse C57BL/60laHsd ob/ob and male mouse C57BL/60laHsd +/?, 4-10 weeks old, from Harlan France).

The ob/ob mouse produces a nonfunctional leptin and has, as a consequence hyperphagia, high obesity, hyperinsulinemia and insulin resistance.

A Northern blot analysis, carried out according to standard protocols, of the total RNA from the white adipose tissue of ob/ob "obese" mouse and of "thin" mouse hybridized with a full-length cDNA probe encoding the SPARC protein revealed two MRNA species of 4 and 2.2 kb, the last being the principal messenger.

In the ob/ob mouse, the two transcripts were induced approximately 4 fold higher than in the control "thin" mouse. This demonstrates that the expression of the SPARC gene is high in the adipose tissue of ob/ob mouse.

These results show that the modulation of the mRNA for SPARC in adipose tissue is not limited to the acquired form of obesity, as in the GTG model, and this expression does not depend on an intact signaling of the leptin.

Apart from the adipose site, the adipose tissue contains various other cell types, including preadipocytes, endothelial cells, smooth muscle cells, fibroblasts, mastocytes and macrophages.

To determine the source of expression of the SPARC protein in the adipose tissue, cell separating experiments were carried out.

To do that, epididymal tissues were collected from ob/ob mouse and from "thin" mouse (+/?), and then treated with a collagenase (Liberase Blendzyme 3 from Roche Molecular Biochemicals, Indianapolis), and then subjected to differential centrifugation in order to separate the adipose cells (supernatant) from the nonadipose cells (vascular stroma fraction in the pellet).

The total RNA was isolated using TRIzol according to the manufacturer's instructions (Life Technologies), RNA quantified by measuring the absorbance at 260 nm.

The quantity of MRNA for SPARC associated with each of these cellular fractions was determined by RT-PCR.

The results show that the majority of the mRNA for SPARC is in the adipocyte fraction and that this expression is higher in the "obese" mouse adipocytes than in the "thin" mouse adipocytes.

The mRNA for SPARC was also detected in the vascular stroma fraction, but to a lesser degree. The expression of SPARC mRNA and its increase in the "obese" mouse adipose tissue is therefore mainly present in the adipocytes.

To grasp more clearly the modulation of the SPARC protein in obesity, the expression of the SPARC gene in a model of obesity induced by a particular diet was studied.

A study of the development of obesity was carried out with an AKR strain predisposed to obesity in response to a diet with a high fat content.

These 5-week old AKR/OlaHsd mice (West et al., (1992). Am. J. Physiol. 262 : R1025-R1032) received either a diet containing 12% of calories derived from fats, or a diet with a high fat content (Teklad Adjusted Calories TD 97363, Harlan Teklad, Madison Wis.) containing 21% by weight of anhydrous milk lipids, corresponds to 42% of calories derived from fat.

During 10 weeks of a diet with a high fat content, these mice were weighed twice per week. After 3, 6 and 10 weeks of a diet, the mice were humanely killed and the epididymal fatty parts were immediately removed, weighed and treated in order to extract the total RNA. The total RNA was isolated using TRIzol according to the manufacturer's instructions (Life Technologies), the RNA is quantified by measuring the absorbance at 260 nm.

For an equal weight at the beginning, after 10 weeks, the mice which received a diet with a high fat content gained 15.3±1.5 g, the other mice which received a normal diet gained 10.5±1.4 g. In addition, the weight of the epididymal fatty parts was four times higher than the mice which received a diet with a high fat content than in those which received a normal diet.

By Northern blot analysis, after ten weeks of these diets, the major SPARC transcript was three times higher in the mice which received a diet with a high fat content than in those which received a normal diet.

In parallel, the expression of the SPARC gene was studied as a function of time, after 3, 6 and 10 weeks on a diet with a high fat content. Between 3 and 6 weeks, the level of mRNA for SPARC increased significantly. After 10 weeks, the level of mRNA for SPARC tended to decrease, but remained higher than that observed after three weeks on the same diet.

Thus, this shows that the level of mRNA is increased in a model of obesity obtained by a specific diet and this increase arrives quite early in the development of obesity.

The increase in the expression of the SPARC gene in the adipose tissue is characteristic of the genetic or acquired obesity induced by hyperphagia or by a diet with a high fat content.

By immunoblot analysis, it was observed that the level of SPARC protein in the adipocytes of ob/ob "obese" mice is 3 to 4 times higher than in the "thin" mice. These results demonstrate that this increase in protein is in agreement with the increase in the expression of its gene.

SPARC is a secreted molecule; an ex vivo analysis of the capacity of the adipocytes to secrete the SPARC protein was carried out.

The concentration of SPARC antigen in a medium conditioned for 16 hours with freshly isolated rat adipocytes was measured by SPARC-specific ELISA. A quantity of SPARC protein approximately seven times higher was observed in the conditioned medium compared with the control medium.

Thus, the mature adipose cells produce and secrete the SPARC protein.

Moreover, it was observed that insulin injected into mice increases the expression of the messenger for the SPARC protein in the adipose tissue.

As the high expression of SPARC in adipocytes is probably associated with the increase in the adipose mass in obesity, a study of the expression of SC1, a protein linked to the SPARC protein, was produced in order to see if this expression was also modulated in the adipose tissue of "obese" mice.

The SPARC proteins and the SC1 proteins (also known under the name of hevin) are obtained from a small family of proteins which are defined by a variable N-terminal domain, followed by two conserved domains, a follistatin-like domain and a calcium-binding domain. The SC1 protein exhibits great similarity with the SPARC protein (70% similarity at the level of the amino acids) and was envisaged to functionally compensate for the deficiency in SPARC protein in the transgenic mice lacking the SPARC gene.

Thus, following RT-PCR analysis, and unlike the mRNA for SPARC, expression of mRNA for SC1 in ob/ob "obese" GTG mice is not increased in these models. This shows that the altered adipocyte expression of SPARC has specific functional consequences in obesity.

The invention claimed is:

1. An in vitro method for screening agents capable of decreasing the level of expression or the activity of SPARC protein in a subject diagnosed as being obese, comprising the following steps:

measuring the level of expression or the activity of the SPARC protein in an extract obtained from an adipose tissue from said subject in the presence and in the absence of the agent to be tested, determining if the level of expression or the activity of the SPARC protein is decreased in the presence of the agent to be tested compared with the level of expression or the activity of the SPARC protein in the absence of the agent to be tested, optionally, identifying the agent which decreases the level of expression or the activity of the SPARC protein.

2. The method as claimed in claim 1, wherein the agent to be tested is contacted with a biological extract and the measurement is then carried out directly, said biological extract being collected before said contacting.

3. The method as claimed in claim 1, wherein the adipose tissue is abdominal adipose tissue or skeletal muscle adipose tissue.

4. The method as claimed in claim 1, wherein the expression or the activity of the SPARC protein of the adipose tissue is measured.

5. A method for screening an agent capable of decreasing the level of expression of or the activity of the SPARC protein in a subject diagnosed as being obese comprising the steps of:

adding an agent to a sample, the sample being one of a collected biological material from said subject and an extract of collected biological material from said subject, the collected biological material comprising adipose tissue;

measuring the level of expression of or the activity of a SPARC protein in the sample in the presence of the agent;

comparing the level of expression of or the activity of the SPARC protein in the sample in the presence of the agent to the level of expression of or the activity of the SPARC protein in the absence of the agent; and identifying the agent as one that is capable of decreasing the level of expression of or the activity of the SPARC protein in a subject diagnosed as being obese if the level of expression of or the activity of the SPARC protein in the presence of the agent is lower than the level of expression of or the activity of the SPARC protein in the absence of the agent.

* * * * *